(12) United States Patent
Bolton et al.

(10) Patent No.: US 7,279,156 B2
(45) Date of Patent: Oct. 9, 2007

(54) APOPTOTIC ENTITIES FOR USE IN TREATMENT OF ENDOTHELIUM DYSFUNCTION DISORDERS

(75) Inventors: Anthony E. Bolton, Dublin (IE); Arkady Mandel, North York (CA); Daniel N. Sauder, Princeton, NJ (US)

(73) Assignee: Vasogen Ireland Limited, Shannon, County Clare (IE)

( * ) Notice: Subject to any disclaimer, the term of this patent is extended or adjusted under 35 U.S.C. 154(b) by 187 days.

(21) Appl. No.: 09/866,569

(22) Filed: May 25, 2001

(65) Prior Publication Data

US 2002/0058023 A1 May 16, 2002

(51) Int. Cl.
G09B 25/08 (2006.01)
A61K 35/00 (2006.01)
A61K 35/12 (2006.01)

(52) U.S. Cl. .................. 424/93.1; 424/93.7; 424/277.1

(58) Field of Classification Search ............... 424/93.7, 424/93.1; 435/2
See application file for complete search history.

(56) References Cited

FOREIGN PATENT DOCUMENTS

| WO | 93/15778 | 8/1993 |
|---|---|---|
| WO | 96/34613 | 11/1996 |
| WO | WO99/58645 | 11/1999 |
| WO | 00/29003 | 5/2000 |
| WO | WO 00/62788 | 10/2000 |

OTHER PUBLICATIONS

Henry F et al Pathobiology 1999; 67(5-6):306-10.*
Dini et al (J Cell Sci. 1995; 108:967-973).*
Yamaoka et al Jpn Circ J. 1999; 63(12):951-956.*
Aukrust et al Ann. Med. 2005;37:74-85.*
Bombeli, T., et al., "Apoptotic Vascular Endothelial Cells Become Procoagulant," *Blood*, 89:2429-2442 (1997).
Buttke and Sandstrom, et al., "Oxidative Stress As a Mediator of Apoptosis," *Immunology Today*, 15:7-10 (1994).
De Caterina, R., "Endothelial dysfunctions: common denominators in vascular disease," *Current Opinions in Lipidology*, 11:9-23, (2000).
Fadok, V.A., et al., "Exposure of Phosphatidylserine on the Surface of Apoptotic Lymphocytes Triggers Specific Recognition and Removal by Macrophages," *Journal of Immunology*, 148:2207-2216 (1992).
Fadok, V. A., et al., "A receptor for Phosphatidylserine-specific clearance of apoptotic cells," *Nature*, 405:85-90 (2000).
Gavrieli, Y., et al., "Identification of Programmed Cell Death In Situ via Specific Labelling of Nuclear DNA Fragmentation," *J. of Cell Biology*, 119:493-501 (1992).
Guijarro, C., et al., "3-Hydrxy-3 Methylglutaryl Coenzyme A Reductase and Isoprenylation Inhibitors Induce Apoptosis of Vascular Smooth Muscle in Culture," *Circulation Research*, 83:490-500 (1998).
Kerr, et al., "Apoptosis: A basic biological phenomenon with wide-ranging implications in tissue kinetics," *British Journal of Cancer*, 26:239-257 (1991).
Kondo, et al., "Lymphocyte Function-Associated Antigen-1 is Required for Maximum Elicitation of Allergic Contact Dermatitis," *Br. J. Dermatol.* 131:354-359 (1994).
Kondo, et al., "Interleukin-10 Inhibits the Elicitation Phase of Allergic Contact Hypersensitity," *The Journal of Investigative Dermatology*, 103:811-814 (1994).
Libby, P., "Changing concepts of atherogenesis," *Journal of Internal Medicine*, 247:349-358, (2000).
Loo, D. T. and Rillema, J.R., "Measurement of Cell Death," *Methods in Cell Biology*, 57:251-264 (1998).
Salvioli, S., et al., "JC-1, but not $DiOC_6(3)$ or Rhodamine 123, is a Reliable Fluorescent Probe to Assess $\Delta\psi$ Changes in Intact Dells: Implications For Studies on Mitochondrial Functionality During Apoptosis," *FEBS Letters*, 411:77-82 (1997).
Susin, S.A., "Mitochondrial Release of Caspase-2 and -9 During the Apoptotic Process," *Journal of Experimental Medicine*, 189:381-394 (1994).
Suzuki, Y., "Cell Death Phagocytosis, and Neurogenesis in Mouse Olfactory Epithelium and Vomeronasal Organ After Colcicine Treatment," *Annals of the New York Academy of Sciences*, 855:252-254 (1998).
Teiger, E., "Apoptosis in Pressure Overload-Induced Heart Hypertrophy in the Rat," *Journal of Clinical Investigation*, 97:2891-2897 (1996).
Bodey, B., et al. "Apoptosis in the Mammalian Thymus During Normal Histogenesis and Under Various In Vitro and In Vivo Experimental Conditions," *In Vivo*, 12(1): 123-134 (1998).
Cooke, E.D., et al. "Treatment of Severe Raynaud's Syndrome by Injection of Autologous Blood Pretreated by Heating, Ozonation and Exposure to Ultraviolet Light (H-O-U) Therapy," *International Angiology*, Torino, It. 16(4): 250-254 (1997).
Ganelina, I.E., et al. "Therapy of Severe Steno Cardias by UV Irradiation of the Blood and Some Action Mechanisms of this Therapy," *Folia Haematologica*, Akademische Verlagsgesellschaft, Leipzig, DE, 109(3):470-482 (1982).
Shivji, G.M., et al. "Effects of VAS972 Therapy on Allergic Contact Hypersensitivity," *Journal of Investigative Dermatology*, New York, NY, 114(4): 862 (2000). (Abstract 675).
M. Marini et al., "Apoptosis of Human Lymphocytes in the Absence or Presence of Internucleosomal DNA Cleavage" *Biochemical and Biophysical Research Communications*, vol. 229, No. 3, 1996, pp. 910-915.
Shivji, G.M., "Effects of VAS972 Therapy on Allergic Contact Hypersensitivity," *J of Investigative Dermatology* 114(4):862 (2000).

* cited by examiner

*Primary Examiner*—Christopher H. Yaen
(74) *Attorney, Agent, or Firm*—Foley & Lardner LLP

(57) ABSTRACT

Treatment and/or prophylaxis of endothelial dysfunction-related disorders in mammalian patients is effected by administering to the patient effective amounts of apoptotic bodies and/or apoptotic cells.

14 Claims, 1 Drawing Sheet

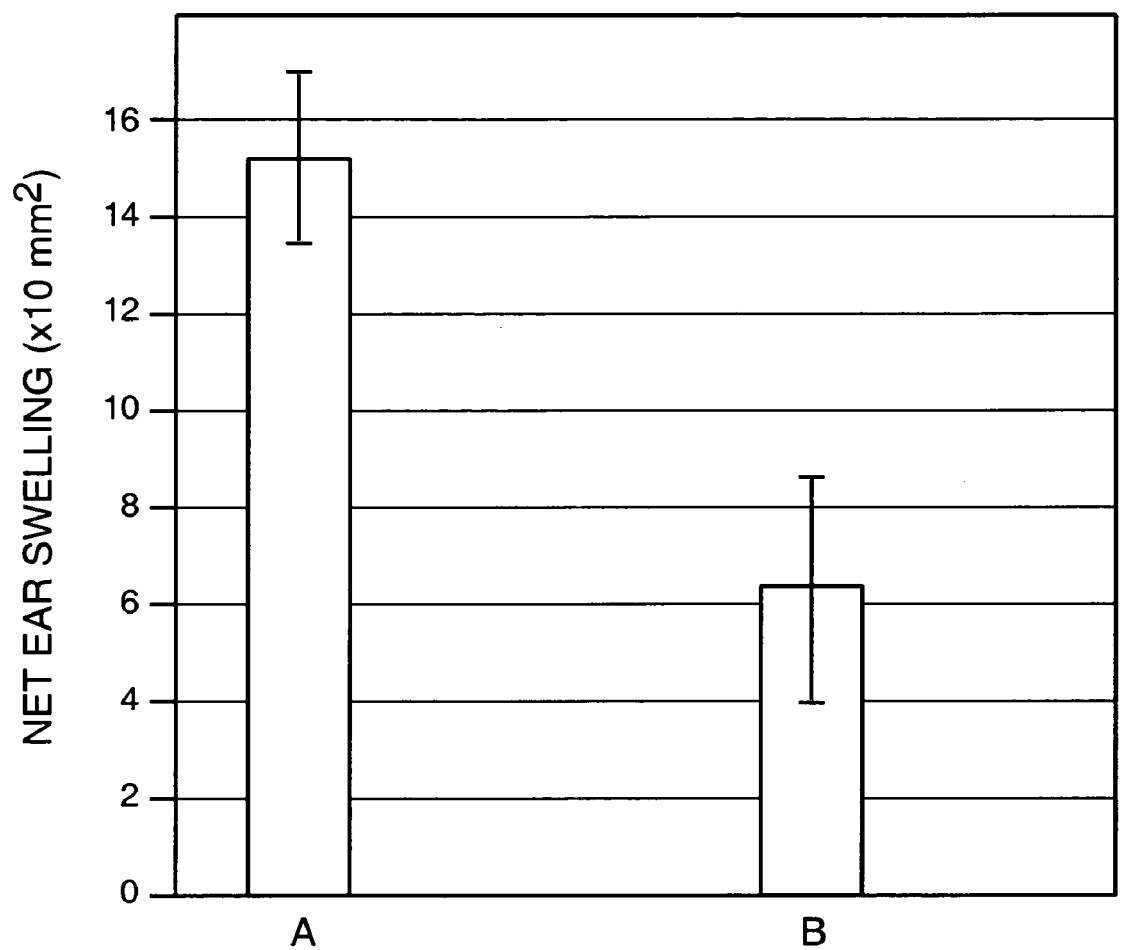
FIGURE

APOPTOTIC ENTITIES FOR USE IN TREATMENT OF ENDOTHELIUM DYSFUNCTION DISORDERS

This application claims priority under 35 U.S.C. §§ 119 and/or 365 to Ser. No. 2,309,417 filed in Canada on May 25, 2000 ; the entire content of which is hereby incorporated by refernce.

FIELD OF THE INVENTION

This invention relates to biochemical and biological compositions and to the uses thereof in the treatment and/or prophylaxis, in mammalian patients, of various medical disorders associated with endothelial dysfunction (malfunctioning of the lining of blood vessels). More particularly, it relates to treatment and prophylaxis of medical disorders associated with endothelial dysfunction by administration of compositions containing mammalian cellular materials and fragments thereof, and to the compositions containing the mammalian cellular materials and fragments themselves, and to processes for preparing such compositions.

BACKGROUND OF THE INVENTION

Two mechanisms of cell death in the body are recognized, necrosis and apoptosis. Apoptosis is the process of programmed cell death, described by Kerr et al in 1992, (Kerr J F R, Wyllie A H, Currie A R (1992). "Apoptosis: a basic biological phenomenon with wide-ranging implications in tissue kinetics. "*British Journal of Cancer* 26: 239–257") by which steady-state levels of the various organ systems and tissues in the body are maintained as continuous cell division and differentiation takes place. Cells undergoing apoptosis often exhibit distinctive morphological changes such as a pronounced decrease in cell volume, modification of the cytoskeletons resulting in pronounced membrane blebbing, a condensation of the chromatin, and degradation of the DNA into oligonucleosomal fragments. Following these morphological changes, an apoptotic cell may break up into a number of small fragments known as apoptotic bodies, comprising membrane-bound bodies containing intact organelles, chromatin, etc. Apoptotic bodies are normally rapidly removed from the body by phagocytosis by macrophages, dendritic cells and other antigen-presenting cells, before they can become lysed and release their potentially pro-inflammatory intracellular contents.

In simple outline, apoptosis is thought to proceed as follows. Three phases can be identified in the apoptotic mechanism of programmed cell death:

Induction phase;
Effector phase; and
Degradation phase.

The induction phase is dependent in part on specific interactions of death-inducing signals at the cell surface membrane. One common signal is initiated by the binding of specific ligands to receptors of the TNF receptor family present on the cell membrane. One important such receptor is Fas (APO-1, CD95), which interacts with Fas-ligand to initiate apoptosis.

The effector phase, activated by the binding of receptors and ligands of the induction phase, leads to the activation of caspases, cystinyl-aspartate-requiring proteinases (proteolytic enzymes), including caspases 1 and 8. This activation may be associated with a change in the permeability of mitochondria, allowing the release of cytochrome-c which is involved in caspase activation. Activated caspases initiate a chain of lethal proteolytic events culminating in the changes in chromatin and cytoskeletal components seen in apoptosis.

Many cells undergoing apoptosis can be identified by a characteristic 'laddering' of DNA seen on agarose gel electrophoresis, resulting from cleavage of DNA into a series of fragments. These changes occur a few hours before death of the cell as defined by the ability of a cell to exclude vital dyes. The appearance of DNA laddering on agarose gel electrophoresis following extraction of DNA from cells is one recognized method of identification of apoptosis in cells (Loo, D. T. and Rillema, J. R. (1998) "Measurement of Cell Death," *Methods in Cell Biology* 57: 251–264), although it is not always sensitive enough to detect apoptosis. In situ labeling of nuclear DNA fragmentation, for example, using commercially available terminal dUTP nick end labeling (TUNEL) assays, is an alternative and more reproducible measure for the determination of fragmented DNA in apoptotic cells and cells undergoing apoptosis (Gavrieli Y, Sherman Y, Ben-Sasson S A (1992) "Identification of programmed cell death in situ via specific labelling of nuclear DNA fragmentation," *Journal of Cell Biology* 119: 493–501).

During apoptosis, phosphatidylserine becomes exposed externally on the cell membrane (Fadok V A, Voelker D R, Campbell P A, Cohen J J, Bratton D L, Henson P M (1992), "Exposure of phosphatidylserine on the surface of apoptotic lymphocytes triggers specific recognition and removal by macrophages". *Journal of Immunology* 148: 2207–2216) and this exposed phosphatidylserine binds to specific receptors to mediate the uptake and clearance of apoptotic cells in mammals (Fadok V A, Bratton D L, Rose D M, Pearson A, Ezekewitz R A B, Henson P M (2000), "A receptor for phosphatidylserine-specific clearance of apoptotic cells", *Nature* 405: 85–90). The surface expression of phosphatidylserine on cells is another recognized method of identification of apoptotic cells.

Changes in mitochondrial integrity are intimately associated with apoptosis, resulting in alterations in mitochondrial membrane permeability and the release of cytochrome-c from the mitochondria into the cell cytoplasm (Susin, S. A., Lorenzo, H. K., Zamzami, N., Marzo, I, Brenner, C., Larochette, N., Prevost, M. C., Aizari, P. M. and Kroemer, G. (1999) "Mitochondrial Release of Caspase-2 and -9 during the Apoptotic Process", *Journal of Experimental Medicine,* 189: 381–394). Measurement of changes in mitochondrial membrane potential, reflecting changes in mitochondrial membrane permeability, is another recognized method of identification of apoptotic cells.

A number of other methods of identification of cells undergoing apoptosis and of apoptotic cells, many using monoclonal antibodies against specific markers for apoptotic cells, have also been described in the scientific literature.

Methods of quantifying apoptotic cells and apoptotic bodies in a cellular composition are known and readily practiced by persons of skill in the art. Techniques include staining of the treated cell population, with an appropriate, selective dye such as fluorescein-conjugated annexin V, followed by incubation and analysis by flow cytometry.

Necrosis, in contrast, is cell death of a pathological nature, resulting from injury, bacterial toxin effects, inflammatory mediators, etc., and involving membrane rupture and release of intracellular contents to the surrounding tissue, often with harmful inflammatory consequences. Necrotic cells may be detected and characterized by detection of compromised cell membranes e.g. by methods such as staining with propidium iodide followed by flow cytometry or microscopy.

SUMMARY OF THE INVENTION

According to the present invention, the administration of apoptotic cells and/or apoptotic bodies previously prepared ex vivo, is used in the prophylaxis and/or treatment of medical disorders in which there is dysfunction of the cells of the endothelium, the cellular lining of blood vessels.

In one of its method aspects, this invention is directed to a method for the treatment of or prophylaxis against an endothelium dysfunction disorder in a mammalian patient, which comprises administering to the patient an effective amount of apoptotic bodies and/or apoptotic cells.

These methods are preferably accomplished by administering to the patient the pharmaceutical compositions described herein.

BRIEF DESCRIPTION OF THE DRAWING

The FIGURE is a graph showing a comparison of net ear swelling in mice treated with the compositions of this invention and a control group.

DESCRIPTION OF THE PREFERRED EMBODIMENTS

This invention is directed to the treatment and/or prophylaxis of endothelium dysfunction disorders by administering apoptotic cells and/or bodies to a mammalian patient.

The endothelium is a cellular layer lining the walls of blood vessels of a mammal. It is a highly specialized interface between blood and underlying tissues and has a number of functions, including: control of haemostasis by inhibiting platelet aggregation (antithrombotic and regulating the coagulation and fibrinolytic systems); control of vascular tone, and hence blood flow; control of blood vessel smooth muscle growth; and selective permeability to cells and proteins.

Normally, the endothelium maintains vascular homeostasis by responding to physiological stimuli, for example, changes in blood flow, oxygen tension etc., by adaptive alteration of function. Dysfunctional endothelium has an impaired response to such physiological stimuli, and can ultimately lead to medical disorders. A number of subsets of endothelial dysfunction have been recognized, including Endothelial Activation, and Endothelial-mediated Vasodilatory Dysfunction (see De Caterina (2000). "Endothelial dysfunctions: common denominators in vascular disease". Current Opinions in Lipidology 11:9–23).

Endothelial activation may lead to the initiation of atherosclerosis and is a process whereby there is an inappropriate up-regulation and expression of cell attraction and cell adhesion molecules on endothelial cells. This particularly involves the Macrophage Chemoattractant Protein-1 (MCP-1), chemoattractants for lymphocytes (IP-10, MIG, I-TAG), and the Vascular Cell Adhesion Molecule-1 (VCAM-1), to which the monocytes and lymphocytes adhere. Once adherent, the leucocytes enter the artery wall. The monocytes and lymphocytes are recruited to the intima (sub-endothelial layers) of the blood vessels by these cell attraction and cell adhesion molecules of the activated endothelium during the early stages of atherosclerosis (see Libby, P. (2000) "Changing concepts of atherogenesis," *Journal of Internal Medicine* 247:349–358.)

Endothelial-mediated Vasodilatory Dysfunction is characterized by a reduction or loss of endothelium-dependent vasodilation and involves "decreased nitric oxide bioavailability" (decreased production, increased destruction and/or decreased sensitivity to nitric oxide). (De Caterina (2000), cited above). Nitric oxide induces vasodilation by relaxing the smooth muscle cells of the blood vessel wall. Endothelial-mediated Vasodilatory Dysfunction can be measured as a reduction in vasodilation in response to acetylcholine, or as a reduced vasodilatory response following occlusion of arterial blood flow (reactive hyperaemia) for example using a sphygmomanometer cuff. As well as leading to a reduction in vasodilation, decreased endothelial nitric oxide bioavailability can also result in an increase in the production of vaso-constriction and hypertension. Platelet aggregation is inhibited by nitric oxide, hence a decrease in nitric oxide bioavailability can lead to an increase in platelet aggregation and consequent thrombosis. These are just a few examples of how decreased nitric oxide bioavailability resulting from Endothelial-mediated Vasodilatory Dysfunction can have pathological consequences.

The medical disorder resulting from endothelial dysfunction, and hence treatable in accordance with the present invention, can be a cardiovascular disorder such as atherosclerosis, peripheral vascular disease, congestive heart failure, stroke, myocardial infarction, angina, hypertension and the like. It can be a vasospastic disorder such as Raynaud's disease, cardiac syndrome X, migraine and the like. It can be the damage resulting from ischemia (ischemic injury or ischemia-reperfusion injury). In summary, it can be substantially any disorder that results from an inappropriately functioning endothelium.

"Apoptotic cells" and "apoptotic bodies," as the terms are used herein, means cells and cell bodies which exhibit one or more of the following apoptosis-characterizing features: surface exposure of phosphatidylserine, as detected by standard, accepted methods of detection such as Annexin V staining; alterations in mitochondrial membrane permeability measured by standard, accepted methods (e.g. Salvioli, S., Ardizzoni, A., Franceschi, C. Cossarizza, A. (1997) "JC-1, but not DiOC6(3) or Rhodamine 123, is a Reliable Fluorescent Probe to assess Delta Psi Changes in Intact Cells: Implications for Studies on Mitochondrial Functionality during Apoptosis," *FEBS Letters* 411: 77–82); evidence of DNA fragmentation such as the appearance of DNA laddering on agarose gel electrophoresis following extraction of DNA from the cells (Teiger, B., Dam, T. V., Richard, L., Wisnewsky, C., Tea, B. S., Gaboury, L., Tremblay, J., Schwartz, K. and Hamet, P. (1996) "Apoptosis in Pressure Overload-induced Heart Hypertrophy in the Rat," *Journal of Clinical Investigation* 97; 2891–2897), or by in situ labeling (see Gavrieli et al., 1992, referenced above).

The compositions of apoptotic cells and/or apoptotic bodies for use in the present invention preferably comprise not more than about 35 weight percent of necrotic cells and/or necrotic bodies based on the total weight of the apoptotic cells/bodies and necrotic cells/bodies; more preferably, not more than about 20 weight percent; and even more preferably, not more than about 10 weight percent. At these levels, the presence of such necrotic cells and/or bodies are believed not to significantly alter in vivo processes. In its most preferred embodiment, the apoptotic cells/bodies are substantially free of necrotic cells and/or bodies (i.e., less than about 2 weight percent of necrotic cells/bodies).

The apoptotic cells and/or apoptotic bodies for use in the present invention are prepared ex vivo from mammalian cells that are compatible with those of the mammalian patient. They can be prepared from substantially any type of mammalian cell including cultured cell lines. Preferably they are prepared from a cell type derived from the mammalian patient's own body or from an established cell line. More preferably they are prepared from white blood cells of blood compatible with that of the mammalian patient, more preferably from the patient's own white blood cells and even more preferably from the patient's own T lymphocytes. Even more preferably they are prepared from an established cell line. The apoptotic cells and/or apoptotic bodies are prepared extracorporeally prior to administration to the patient. Thus, in one embodiment, an aliquot of the patient's blood may be withdrawn, e.g. by venipuncture, and at least a portion of the white cells thereof subjected extracorporeally to apoptosis inducing conditions.

A variety of methods of inducing apoptosis in mammalian cells, so as to create apoptotic cells and/or apoptotic bodies, are known in the art and essentially any of these can be adopted in preparing apoptotic bodies for use in the present invention. One such method is the subjection of the cells to ionizing radiation (γ-rays, x-rays, etc.) and/or non-ionizing electromagnetic radiation including ultraviolet light. Apoptosis can be induced by subjecting cells to ultrasound.

Another method is the treatment of the cells with drugs such as non-specific protein kinase inhibitors as exemplified by staurosporine (see Bombeli, Karsan, Tait and Hirlan, (1997) "Apoptotic Vascular Endothelial Cells Become Procoagulant", *Blood*, Vol. 89:2429–2442). Also, certain chemotherapeutic agents used for the treatment of malignant tumours induce apoptosis, for example, adriamycin, as can statin drugs (3-hydroxy-3methylglutaryl coenzyme A reductase inhibitors) (Guijarro C, Blanco-Colio L M, Ortego M, Alonso C, Ortiz A, Plaza J J, Diaz C, Hernandez G, Edigo J (1998), "3-hydroxy-3methylglutaryl coenzyme A reductase and isoprenylation inhibitors induce apoptosis of vascular smooth muscle in culture," *Circulation Research* 83: 490–500) and colcicine (Suzuki Y (1998)", "Cell death, phagocytosis and neurogenesis in mouse olfactory epithelium and vomeronasal organ after colcicine treatment," *Annals of the New York Academy of Sciences* 855: 252–254). The use of ligands for death receptors on cells, such as Fas-ligand, will be apparent for inducing apoptosis from the discussion of apoptosis above. A further method is the application of oxidative stress to cells extracorporeally (see for example Buttke and Sandstrom (1994) "Oxidative Stress as a Mediator of Apoptosis,"*Immunology Today*, Vol. 15:7–10). This can be achieved by treating the cells, in suspension, with chemical oxidizing agents such as hydrogen peroxide, other peroxides and hydroperoxides, ozone, permanganates, periodates, and the like. Biologically acceptable oxidizing agents are preferably used, so as to reduce potential problems associated with residues and contaminations of the apoptotic cells and/or apoptotic bodies so formed.

The present invention is not restricted to any particular method of producing apoptotic cells and/or apoptotic bodies, for use herein, and any suitable, known process can be used.

Methods for the detection and quantitation of apoptosis can be used to determine the presence and level of apoptosis in the preparation to be administered to the patient in the present invention. A method as described in the introduction above should be used to confirm the level of apoptosis achieved prior to administration. They are suitably purified prior to use, by methods known in the art, such as differential centrifugation.

In preparing the apoptotic cells and/or apoptotic bodies, care should be taken not to apply excessive levels of oxidative stress, radiation, drug treatment, etc., since otherwise there is a significant risk of causing necrosis of at least some of the cells under treatment. Necrosis causes cell membrane rupture and the release of cellular contents often with biologically harmful results, particularly inflammatory events, so that the presence of necrotic cells and their components along with the apoptotic bodies is best avoided. Appropriate levels of treatment of the cells to create apoptotic bodies for use in the present invention depend to some extent on the nature of the chosen cells and cellular composition, and the type of treatment chosen to induce apoptosis. Such appropriate levels are readily determinable by those skilled in the art, having regard to the available scientific literature on the subject including the above-reference articles.

One preferred process according to the present invention involves the culture of cells from the patient, or a compatible mammalian cell line. The cultured cells may then be treated to induce apoptosis and to create apoptotic cells and/or apoptotic bodies therein. The cells, suspended in the patient's plasma or another suitable suspension medium, such as saline or a balanced mammalian cell culture medium, can then be administered as indicated below. The numbers of apoptotic cells and/or bodies can be determined by published methods available in the scientific literature on the subject including the above-reference articles. The numbers of such apoptotic cells and/or apoptotic bodies required for administration to the patient to obtain the required clinical benefit will vary depending on the source of cells, the patient's condition, the age and weight of the patient and other relevant factors which are readily determinable by the attending clinician.

Another example of a preferred process according to the present invention accordingly involves extraction of an aliquot of blood from the patient to be treated, separation of the white cells therefrom, suspension of the white cells in plasma or another suitable suspension medium, such as saline or a balanced mammalian cell culture medium and treatment of the white cells under apoptosis-causing conditions, e.g. with a chemical such as sodium butyrate, so as to create a cellular composition in which significant numbers of the white cells therein have been apoptosed so as to create therein substantial numbers of apoptotic cells or bodies. Then the treated composition is re-administered to the patient. More preferably, T lymphocytes, isolated from the blood by known means, and suspended as above, may be used as a source of apoptotic cells and apoptotic bodies.

The number of viable cells selected for treatment to create apoptotic cells and/or apoptotic bodies is suitably up to about $4 \times 10^9$, preferably from about 1,000,000 to about 1,000,000,000 and most preferably from about 50,000,000 to about 150,000,000, for each administration to a human patient. From about 10% to 90%, preferably from about 30% to 70% of the cellular compositon for administration is comprised of apoptotic cells and apoptotic bodies, the balance being viable cell and necrotic cells. Accordingly, the preferred amounts of apoptotic cells and/or apoptotic bodies for administration are those produced by subjecting these numbers of cells to the apoptosing conditions. When whole blood is used as the source of the cells to be subjected to the apoptosis inducing conditions, these numbers of white cells are obtainable in blood aliquots of volume up to about 400 mls, preferably up to 100 mls. More specifically, 50,000,000 to 150,000,000 cells is equivalent to the white cells in blood aliquots of volume 10–30 mls.

The volume of the aliquot of blood withdrawn from the patient for treatment to create apoptotic cells and/or apoptotic bodies therein is suitable up to about 400 ml, preferably from about 0.1 to about 100 ml, and most preferably from about 5 to about 15 ml. Accordingly, the preferred amounts of apoptotic cells and/or apoptotic bodies for administration are those corresponding to the numbers derivable from the white blood cells, or isolated T lymphocytes, contained in such quantities of whole blood, following subjection to apoptosis-inducing conditions.

The suspension of treated apoptotic cells and/or bodies for administration to the patient is prepared in a biologically acceptable liquid suspending medium, such as the patient's serum or plasma, saline or balanced mammalian cell culture medium. The addition of other factors, such as cytokines, hormones, products of stressed cells or other appropriate biologically active material may enhance the benefit of the administered apoptotic cellular materials. The aliquot can be re-introduced into the patient's body by any suitable method, most preferably intramuscular injection but also including subcutaneous injection, mini-grafting, intra-peritoneal injection, intra-arterial injection, intravenous injection and oral administration. The apoptotic entities can be delivered to the specific body organ and/or site by using any appropriate, known delivery system.

The compositions of this invention may optionally include a pharmaceutically acceptable excipient. Some examples of suitable excipients include sterile water, sterile saline, phosphate buffered saline, and the like.

When administered, the pharmaceutical compositions comprise an effective amount of apoptotic bodies/cells to induce a suitable prophylactic and/or therapeutic response in the patient at risk of suffering or suffering from an endothelial dysfunction related disease. Preferably, the composition administered to the mammalian patient comprises from about 10,000 to 10,000,000 apoptotic cells or bodies per kilogram of body weight, more preferably from about 500,000 to 5,000,000 and most preferably from about 1,500,000 to 4,000,000 apoptotic cells or bodies per kg body weight. The specific dose employed will, of course, be dependent upon the age, weight and severity of the disease in the treated patient all of which are within the skill of the attending clinician.

For most effective treatment and prophylaxis of mammalian disorders involving an endothelial dysfunction, the patient may be given a course of treatments with apoptotic cells and/or bodies according to the invention. Each course of treatment may involve administration to the patient of from 1 to 6 aliquots of suspended cellular material, as described above. No more than one such aliquot should be administered per day, and the maximum rest period between any two consecutive administrations should be not greater than about 21 days. Booster treatments as described below may advantageously be used. To maintain the desired effects, the patient may undergo booster treatments, with a further course of administration of aliquots of suspended apoptotic cells and/or apoptotic bodies as described above, at intervals of three to four months.

As noted, the present invention is applicable to the treatment and/or prophylaxis of a wide variety of mammalian disorders that involve endothelial dysfunction. These include, but are not limited to, cardiovascular disease, such as atherosclerosis, peripheral vascular disease, congestive heart failure, stroke, myocardial infarction, angina, hypertension, etc., vasospastic disorders such as Raynaud's disease, cardiac syndrome X, migraine, etc; and the damage resulting from ischemia (ischemic injury or ischemia-reperfusion injury). In summary it can be substantially any disorder that results from an inappropriately functioning endothelium.

The invention is further described, for illustrative purposes, in the following specific examples.

EXAMPLE 1

Experiments to demonstrate the invention were conducted on laboratory mice, under approved conditions for conducting such experiments.

The effectiveness of the treatment according to a preferred embodiment of the present invention, on contact hypersensitivity (CHS), an example of a Th-1-cell inflammatory disorder which is known to be mediated by inflammatory cytokines, was assessed on laboratory mice, according to approved animal experimentation procedures, using the method described by Kondo et. al., "Lymphocyte function associated antigen-1 (LFA-1) is required for maximum elicitation of allergic contact dematitis" Br. J. Dermatol. 131:354–359 (1994), with minor variations. The disclosure thereof is incorporated herein by reference. Briefly, to induce CHS, the abdominal skin of each mouse was shaved and painted with dinitrodifluorobenzene DNFB, the sensitizing chemical, using 25 µl of 0.5% DNFB in 4:1 acetone: olive oil solution. This sensitization was applied to two groups of Balb/c mice, 10 animals in total.

Apoptotic bodies were prepared from murine fibroblasts. The murine fibroblasts were treated with 50 mM sodium butyrate in RPMI medium, at confluency for one day, and then the sodium butyrate medium was changed. To increase the number of apoptotic cells and bodies, the cells can additionally be irradiated with UV-light (e.g. 75 mj). Supernatant containing floating cells is removed 24 hours following irradiation.

Apoptotic bodies were quantitated by centrifuging the supernatant (1200 rpm, 5 minutes), aspirating the supernatant, washing the resulting cell pellet with PBS and centrifuging again, as above. The pellet containing the apoptotic bodies was re-suspended in PBS. The cells were stored in PBS at 4° C. for the duration of the experiment. The cells to be stained for quantitation were re-suspended in 1× binding buffer at a concentration of $1\times10^6$ cells/ml. 100 µl of the cells were transferred to a 5 ml tube, and 10 µl of fluorescein-conjugated annexin V and 10 µl propidium iodide reagent was added. The cells were gently vortexed and the cell mixture incubated for 15 minutes at 25° C. in the dark. Following the incubation, 400 µl of 1× binding buffer was added to each tube. The sample was analyzed on a flow cytometer over one hour.

Of the two groups of sensitized mice, the first, control group A, received no treatment. The second, test group B, was treated with an injection of suspended apoptotic bodies prepared as described above, 50 µl volume containing at least 150,000 bodies per injection of blood subjected to stressors as described above. Treatments, each involving intramuscular injection of 50 µl of the respective liquid, started on the day of sensitization and were repeated every day for a total of six days. On the same day as the last treatment, but after its administration, the animals were challenged with DNFB, by applying to the right ear of each animal 10 µl of 0.2% solution of DNFB in acetone and olive oil. To the left ear of each animal was applied the acetone/olive oil solvent, without DNFB. Inflammation due to CHS manifests itself in a swelling of the right ears. Ear thickness was measured, 24 hours after challenge, with a Peacock spring-loaded micrometer (Ozaki Co., Tokyo, Japan). The results were expressed as the thickness and difference in thickness of the right ears and the left ears of each animal, at 24 hours after challenge.

The experiments were repeated, using more sets of two groups of animals, a sufficient number of times to ensure statistical significance in the results. A notable and significant reduction in ear thickness (inflammation) was observed with the animals treated with the apoptotic cells and apoptotic bodies suspension in accordance with the invention, as compared with the untreated group, demonstrating a significant reduction in inflammation. The results are presented in the following Table, and on the accompanying FIGURE, as a bar graph of net ear swelling (difference between right ear and left ear thickness), for each group, with "standard deviation" shown by the vertical line at the top of each column.

TABLE 1

| Group | Left ear | Right ear | Difference |
|---|---|---|---|
| A | 17 | 31 | 14 |
| A | 18 | 39 | 21 |
| A | 17 | 30 | 13 |
| A | 18 | 32 | 14 |
| A | 18 | 31 | 13 |
|   |    |    | Mean: 15 |
|   |    |    | S.D: 3.391165 |
| B | 21 | 31 | 10 |
| B | 18 | 18 | 0 |
| B | 17 | 30 | 13 |
| B | 20 | 24 | 4 |
| B | 18 | 22 | 4 |
|   |    |    | Mean: 6.2 |
|   |    |    | S.D.: 5.215362 |

An analysis of the suspension of apoptotic cells and bodies administered to the animals of test group B indicated the presence therein of approximately 40% apoptotic cells and bodies, balance viable cells and minor amounts of necrotic cells (not more than 20%), the presence of which is believed not to be significant in the in vivo process.

EXAMPLE 2

The above test procedure was repeated on similar groups of animals, a control group and a test group, but using a suspension of apoptotic cells and bodies on the test group which comprised about 60% apoptotic cells and bodies, balance viable cells and a minor amount (not more than 20%) of necrotic cells. Essentially similar results were obtained.

The effectiveness of the processes and compositions of the present invention in preventing and alleviating inflammation due to CHS indicates that administration of apoptotic cells and bodies as described up-regulates the in vivo generation of anti-inflammatory Th-2 derived cytokines such as IL-10 (known to be implicated in CHS—see Kondo, McKenzie and Sauder, "The Journal of Investigative Dermatology," Vol. 103, 1994, page 811–814) and/or down-regulates Th-1 inflammatory cytokines such as TNFγ, IL-6 and IL-12. These inflammatory cytokines are implicated in endothelial dysfunctions which manifest themselves as cardiovascular disorders, such as atherosclerosis, peripheral vascular disease, congestive heart failure, stroke, myocardial infarction, angina, hypertension and the like; vasospastic disorders such as Raynaud's disease, cardiac syndrome X, migraine and the like; and damage resulting from ischemia (ischemic injury or ischemia-reperfusion injury). Consequently, the finding of success in CHS treatment reported in the above Examples is indicative of successful use of the process and compositions in the treatment and prophylaxis of a wide variety of endothelial dysfunction disorders including those discussed above.

What is claimed is:

1. A method for treatment of congestive heart failure in a mammalian patient suffering therefrom, which method comprises administering to the patient a congestive heart failure treating effective amount of apoptotic bodies, wherein said apoptotic bodies exhibit at least two characteristics comprising DNA fragmentation, surface exposure of phosphatidylserine, or altered mitochondrial membrane permeability, with consequent alleviation of patient's symptoms of congestive heart failure.

2. The method of claim 1 wherein the apoptotic bodies are in a liquid suspension along with viable cells.

3. The method of claim 2 wherein the apoptotic bodies comprise from 10% to 90% of the cellular portion of the suspension.

4. The method of claim 3 wherein the apoptotic bodies comprise from 30% to 70% of the cellular portion of the suspension.

5. The method of claim 3 wherein the apoptotic bodies are derived from extracorporeal treatment of blood cells compatible with those of the mammalian patient.

6. The method of claim 1 wherein the apoptotic bodies are derived from established cultured cells.

7. The method of claim 5 wherein the blood cells are white blood cells of blood compatible with that of the mammalian patient.

8. The method of claim 7 wherein the blood cells are the patient's own white blood cells.

9. The method of claim 8 wherein the blood cells are the patient's own T lymphocytes.

10. The method of claim 1 wherein the effective amount of apoptotic bodies comprises from 10,000 to 10,000,000 apoptotic bodies per kilogram body weight of the patient, administered as a dosage.

11. The method of claim 10 wherein the dosage contains from 500,000 to 5,000,000 apoptotic bodies per kilogram body weight of the patient.

12. The method of claim 10 wherein the dosage contains from 1,500,000 to 4,000,000 apoptotic bodies per kilogram body weight of the patient.

13. The method of claim 10, wherein the mammalian patient is a human.

14. A method for treatment of congestive heart failure in a mammalian patient suffering therefrom, which method comprises administering to the patient a congestive heart failure treating effective amount of apoptotic bodies, wherein said apoptotic bodies exhibit at least two characteristics comprising the binding of Fas ligands to Fas receptors, caspase activation, DNA fragmentation, surface exposure of phosphatidylserine, altered mitochondrial membrane permeability, or release of mitochondrial cytochrome-c, with consequent alleviation of patient's symptoms of congestive heart failure.

* * * * *

UNITED STATES PATENT AND TRADEMARK OFFICE
CERTIFICATE OF CORRECTION

PATENT NO. : 7,279,156 B2
APPLICATION NO. : 09/866569
DATED : October 9, 2007
INVENTOR(S) : Anthony E. Bolton, Arkady Mandel and Daniel N. Sauder It is certified that error appears in the above-identified patent and that said Letters Patent is hereby corrected as shown below:

In Column 2, line 42, please replace "Aizari" with --Alzari--;

In Column 4, line 5, please replace "acetyicholine" with --acetylcholine--;

In Column 9, line 55, please replace "peripheal" with --peripheral--.

Signed and Sealed this

Eighth Day of April, 2008

JON W. DUDAS
*Director of the United States Patent and Trademark Office*